United States Patent [19] [11] 4,146,560
Larkin et al. [45] Mar. 27, 1979

[54] CATALYST PELLET STABILIZATION IN THE PREPARATION OF POLYAMINES FROM POLYNITRILES

[75] Inventors: John M. Larkin; Philip H. Moss, both of Austin, Tex.

[73] Assignee: Texaco Development Corp., New York, N.Y.

[21] Appl. No.: 855,516

[22] Filed: Nov. 28, 1977

Related U.S. Application Data

[63] Continuation-in-part of Ser. No. 763,394, Jan. 28, 1977, abandoned.

[51] Int. Cl.$^2$ .................. C07C 85/00; C07C 89/00
[52] U.S. Cl. .................. 260/583 P; 252/470; 260/584 R; 544/358
[58] Field of Search .......... 260/583 K, 584 R, 583 P; 252/430, 470

[56] References Cited

U.S. PATENT DOCUMENTS

| 3,235,600 | 2/1966 | Evans | 260/583 P |
| 3,384,666 | 5/1968 | Lichtenwalter | 260/583 P |
| 3,673,251 | 6/1972 | Frampton et al. | 260/583 K X |
| 3,891,707 | 6/1975 | Waddan | 260/583 P X |
| 3,972,938 | 8/1976 | Voges et al. | 260/583 P |

Primary Examiner—Winston A. Douglas
Assistant Examiner—John Doll
Attorney, Agent, or Firm—Carl G. Ries; Thomas H. Whaley; James L. Bailey

[57] ABSTRACT

Covers a process for preparing polyamines from the corresponding polynitriles via a pelleted cobalt-copper-chromium hydrogenation catalyst which comprises contacting a polynitrile with hydrogen in presence of said catalyst and a stabilizing agent comprising a polyamine or a hydroxyl-amine whereby catalyst pellet disintegration is inhibited by the presence of said stabilizing agent.

18 Claims, No Drawings

CATALYST PELLET STABILIZATION IN THE PREPARATION OF POLYAMINES FROM POLYNITRILES

CROSS-REFERENCE TO RELATED APPLICATION

This application is a continuation-in-part of Ser. No. 763,394, filed Jan. 28, 1977, now abandoned.

BACKGROUND OF THE INVENTION

1. Field of the Invention

This invention relates to a process of producing polyamines from polynitriles using a hydrogenation catalyst in pellet form whereby said pellets are protected from disintegration.

2. Description of the Prior Art

It has been found that some hydrogenation catalysts in pelleted form when used in the hydrogenation of nitriles to corresponding amines tend to disintegrate. During the hydrogenation reaction the catalyst pellets are swollen or disintegrate into fine particles or both phenomenon occur. Due to loss of physical integrity, usefulness of catalyst pellets suffers somewhat in terms of proper control, particularly in a continuous process where such variables as space velocity, etc. must be carefully considered and controlled. Specifically, channeling occurs in the catalyst bed, so there is improper contact of nitrile with catalyst. Also fine particles sometimes plug the reactor or reactor lines.

In U.S. Pat. No. 3,384,666 a method of inhibiting catalyst pellet disintegration is set out. Essentially this method involves use of a sodium, lithium or potassium hydroxide or alkoxide base. While such expedient use of caustic stabilizer has been found efficacious nevertheless we have subsequently discovered certain drawbacks emanating from such use. For example, it has been found that such a process to be efficiently worked must involve neutralizing the caustic and filtering off the salt. This, of course, involves a time consuming, and relatively expensive additional step. In addition, we have particularly discovered here that the caustic reacts with those nitriles which additionally contain an oxy group in a manner such that the desired amine is not obtained. That is, undesirable side reactions occur. We have therefore discovered an improved process of maintaining hydrogenation catalyst pellet integrity of the cobalt-copper-chromium catalyst type without resort to caustic materials.

SUMMARY OF THE INVENTION

In accordance with the invention, a method of inhibiting disintegration of a cobalt-copper-chromium hydrogenation catalyst in pellet form used to hydrogenate polynitriles to polyamines has been discovered. In its broadest aspects, the invention involves use of a specific class of stabilizing agents comprising a polyamine or hydroxyl-amine whereby such catalyst pellet disintegration is inhibited by the presence of said stabilizing agent.

DETAILED DESCRIPTION OF THE PREFERRED EMBODIMENTS

In more detail, the hydrogenation technique of preparing polyamines from polynitriles via the process of the invention involves hydrogenation of the polynitrile in presence of the above described hydrogenation catalyst in pellet form and at least a stabilizing amount of a specific type of a polyamine or hydroxyl-amine. By use of the term "polyamine" is meant an organic compound containing at least two basic nitrogen atoms. By the term "hydroxyl-amine" is meant an organic compound containing at least one such amino group, and at least one additional hydroxyl group. The amine-hydroxy compound may contain two or more amine groups in conjunction with the hydroxyl group or, alternatively, may contain two or more hydroxyl groups in conjunction with one or more amino groups. The polyamine or hydroxyl-amine stabilizers found useful here are compounds wherein the hydroxyl or amino functional groups are separated by four carbons or less in the molecule, more preferably by three or less carbons and most preferably are separated by 1-3 carbon atoms.

The hydrogenation reaction itself is carried out in liquid phase. In one expedient, the amine stabilizer is added in an amount such that it can also act as a solvent for the polynitrile to be transformed into a polyamine. This is particularly desirable where the polynitrile is a normally solid compound at room temperature and/or at reaction temperature. However, only relatively small amounts of stabilizer need be present to effectively inhibit pellet disintegration and maintain proper physical integrity thereof. Usually, the amount of stabilizer necessary is at least 0.5 percent based on the weight of the polynitrile to be hydrogenated. Particularly when used as all or part of the solvent system the stabilizer may be present in amounts as high as 10 mols per mol of nitrile compound without in any way affecting the efficiency of the process, and, in fact, such molar excesses are particularly preferred when the stabilizer has the dual function of a solvent.

The hydrogenation reaction itself may be run in presence or in the absence of a solvent other than the amine stabilizer-solvent when so employed for the latter function. When an extraneous solvent is used, it is preferred that an organic solvent such as an alcohol be employed. Typical useful alcohols include methanol, ethanol, isopropanol, t-butanol, n-propyl alcohol, and other alcohols, particularly water-miscible alcohols. The organic solvent may be employed in its solvating role as the sole solvent or in conjunction with the liquid stabilizer, also acting as a solvent.

The polynitrile to be treated in accordance with the present invention may be chosen from a wide variety of known materials of this type. Preferred and di- and trinitriles prepared by reacting acrylonitrile with an amine, polyamine, polyhydroxy-monoamine, polyhydroxy-polyamine, etc. such as ammonia, methylamine, piperazine, ethylenediamine, monoethanolamine, diethylene triamine, 3-amino-propanol, methylethanolamine, aminoethylethanolamine, etc. Other preferred polynitriles are those which additionally contained an oxy group. Typcially these oxynitriles include, for example, acrylonitrile adducts of polyols such as ethylene glycol, di- and tri-ethylene glycol, glycerol, trimethylol propane, butane-1,4-diol, butane-1,3-diol etc.

Likewise, the amine stabilizer may be chosen from a wide variety of materials as long as they fall within the broad classes defined above. Such amine stabilizers may include polyamines such as ethylenediamine, tetramethylenediamine, N,N',-dimethyl piperazine, N-ethylpiperazine 1,2-cyclohexyldiamine, diethylenetriamine, triethylenetetramine, piperazine, etc. Appropriate amine-hydroxy stabilizers may, for example, include monoethanolamine, N-nonylethanolamine, diethanolamine, triethanolamine, 1-amino-2-propanol, 3-amino-1- propanol, 1-amino-1-phenyl-2-propanol, 1-amino-1-phenyl-3-propanol, 1-amino-2-phenyl-2-heptanol, 4-phenyl-3-amino-2-butanol, 1-amino-2-benzyl-2-propanol, 1-amino-2-octanol, 1-amino-2-cyclohexyl-2-propanol, methylethanolamine, aminoethylethanolamine, isobutanolamine, 2-(2-aminoethoxy) ethanol and the like.

Greatly preferred stabilizers are those wherein the hydroxy or amino functional group are on adjacent carbon atoms or separated by no more than one or two additional carbon atoms. These may be depicted by the skeleton formula:

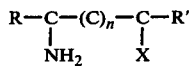

where R, and R′ = alkyl, H or other aromatic or non-aromatic cyclic or open chain organic radicals; n is an integer and = 0–2; and X - $NH_2$ or OH.

Alkoxylated derivatives of any of the foregoing compounds may also be used as stabilizers such as ethylene and propylene oxide adducts of the amine or amino alcohols recited above or others. Such adducts are conventionally made such as set out in U.S. Pat. No. 3,798,184 describing aminoalkylation, which technique may also be applied here in a variety of ways.

The pelleted catalyst protected here from disintegration is a pelleted cobalt-copper-chromium hydrogenation catalyst which consists essentially of about 50–80 percent cobalt, about 10 percent to 49 percent copper, and about 1 percent to about 10 percent chromium, based upon the weight of the metals only. The metals are usually in oxide form.

The support or carrier used may be any one inert to process conditions such as refractory support, charcoal, silica, alumina and the like which are capable of being employed with the active hydrogenation catalysts. The methods of preparing such catalysts on supports are well-known in the art.

The hydrogenation reaction itself may be carried out over a wide range of conditions. Typically, the polynitrile is hydrogenated in the presence of a catalyst of the class described at a temperature within the range of from about 60° to about 200° C. and at a pressure of about 30 to 800 atmospheres in the additional presence of hydrogen. The reaction temperature is more preferably 80°–150° C. with the pressure more preferably being 1000–10,000 psig and most preferably 1000–3000 psig.

In a greatly preferred embodiment, ammonia is also present during the reaction. The ammonia aids the reaction in promoting better selectivity to primary amine, and prevents bimolecular coupling to produce secondary amine formation, usually unwanted in the reaction. When ammonia is present, usually there are about from about 2 to about 20 mols of ammonia present per equivalent of nitrile. When hydrogen and ammonia are used together, the hydrogen partial pressure will usually amount to from about 60 to about 80 percent of the total pressure.

The particular space velocity of the hydrogenation reaction (grams nitrile/hour/cc catalyst) is not critical in the process. However, we prefer to conduct the hydrogenation reaction at a velocity of between about 0.5 to about 5 grams total liquid feed/hour/cc catalyst.

The hydrogenation reaction here can be performed in either a batch or a continuous manner, with the latter being preferred. For this, suitable reactors include either a closed autoclave resulting in a batch process, or a tubular reactor which can be operated in a continuous manner.

The desired polyamine product can then be recovered from the hydrogenation reaction media by any technique known in the art, such as by distillation. Thus, usually the polyamine product must be separated from the amine stabilizer by distillation when the latter is used in amounts such that it also acts as a solvent for the hydrogenation reaction.

This invention will be further illustrated by the following examples which are intended to be illustrative only and are not to be construed to place limitations on the scope of this invention.

EXAMPLE 1

Hydrogenation of N,N′-Bis(cyanoethyl) Ethylenediamine (BCEEDA) In Ethylenediamine (EDA)

A solution of 800 g BCEEDA, 835 g of ammonia, and 1200 g of EDA was continuously charged at 24 ml/hr. through 25 ml of a pelleted catalyst of cobalt, copper and chromium oxides having approximately 75 percent cobalt, 22 percent copper, and 3 percent chromium (based on the weight of the metals only) with 75 percent $H_2$-25 percent $N_2$ flow at 12 liters/hr in a tubular reactor. The reactor was operated for 120 hours at a temperature of 115° C. and pressure of 2500 psig. Effluent samples were colorless through the run; and analyses (IR and GLC) indicated high conversion to bis(aminopropyl)ethylenediamine. The cylindrical tablets of catalyst used (3/16″ × ⅛″) at the conclusion of the run appeared as initially charged with practically no fine particles. On the other hand, when the same polynitrile was hydrogenated with the same catalyst, and under essentially the same conditions without benefit of amine stabilizer and in methanol solvent, the flow through the reactor was stopped by extensive catalyst pellet disintegration after only about 28 hours of operation.

It was also interesting to note that in another comparison run where a typical conventional chemical chelating agent was run, namely, ethylenediaminetetraacetic acid, under essentially the same conditions (present in 0.1–0.15% concentration in methanol), the reactor could be run for only about 48 hours after which time it began to plug because of catalyst disintegration. In addition the effluent was highly colored throughout the run.

EXAMPLE 2

Hydrogenation of Bis(cyanoethyl)diethylene Glycol (BCEDEG) in EDA

The procedure of Example 1 was repeated except that the feedstock consisted of essentially equal parts by weight of BCEDEG, EDA, and $NH_3$. The reactor was run for 128 hours. Infrared analysis indicated only a small amount of unreacted nitrile throughout the run. The used catalyst was in excellent condition; there were no fine particles and the pellets appeared in a hard "like-new" condition.

EXAMPLE 3

Hydrogenation of BCEDEG in Ethanolamine

A solution of 887 g BCEDEG, 1061 g of ethanolamine, and 1017 g of $NH_3$ was charged to 25 ml of cobalt pellets contained in a reactor as in Example 1.

Samples collected throughout the run showed low amounts of unreacted nitrile. The amount of bis-(aminopropyl)diethylene glycol after 17 hours was 72.5% of the hydrogenated products. The used catalyst appeared in excellent condition after 128 hours; pellets were firm and hard (but with a granular surface), and no fine material was present.

EXAMPLE 4

Hydrogenation of Imino(bis)propionitrile (IBPN) In 1,3-propanediamine (PDA)

The procedure of Example 1 was repeated except that the feedstock consisted of essentially equal parts by weight of PDA, NH$_3$, and IBPN. (The latter material may contain about 8 percent of nitrilo(tris)propionitrile according to titrimetric analysis.) All samples throughout the run (120 hrs.) were clear and colorless. The amount of nitrile was at a low level except for the last sample at the end of 120 hours. The catalyst appeared in very good condition with some minimal fine material present.

EXAMPLE 5

Hydrogenation of Bis(cyanoethyl)diaminocyclohexane in DACH (1,2-diaminocyclohexane)

The procedure of Example 1 was repeated except that the feedstock consisted of bis(cyanoethyl)-1,2-diaminocyclohexane, 1100 g of DACH, and 1071 g of NH$_3$. The reactor was operated for 147 hours. Infra-red analysis of the product indicated good conversion of the nitriles to amines. The used catalyst appeared in excellent condition (like new) with no fine material present.

EXAMPLES 6-8

Here the procedure of Example 1 was followed using various substrates and stabilizers. Results are as follows:

TABLE I

| Substrate | Stabilizer | Duration of Run | Catalyst Condition |
|---|---|---|---|
| IBPN | EDA | 238 Hrs. | Very good, small amount of fines |
| Mixture of bis and tris cyanoethyl ethylenediamine | EDA | 128 Hrs. | Very good, small amount of fines |
| Mixture of bis and tris cyanoethyl ethylenediamine | Diethylene triamine | 98 Hrs. | Very good, slightly finer catalyst particles than in above two cases |

EXAMPLE 9

Here, the procedure of Example 1 was run with the exception that no ammonia was used. Even in absence of ammonia the hydrogenation reaction proceeded to a very desirable manner in that a 99% conversion of bis(cyanoethyl) ethylenediamine was effected. In this example there was produced approximately only 4% of amino ethyl bis(aminopropyl) ethylenediamine, demonstrating the fact that the ethylenediamine, even when used as a solvent, and thus present in greatly excessive molar amounts with respect to the biscyano material did not react to any appreciable degree with the biscyano material.

EXAMPLE 10

Here the desirablity of using a colbalt-copper-chromium catalyst in order to convert polynitriles in the process of the invention was demonstrated. In this run a cobalt catalyst was utilized rather than the cobalt-copper-chromium catalyst of Example 9. The specific catalyst employed was a 60% cobalt on kieselguhr. The operating conditions were similar to that of Example 9 with the exception that pure hydrogen replaced the hydrogen/nitrogen mixture. Conversion of bis(cyanoethyl) ethylenediamine was only 73% compared to the approximate 99% conversions of Example 9. In addition, it was noted that the ethylenediamine stabilizer present also tended to react with the material being hydrogenated to a much greater extent. Specifically, the ratio of aminoethyl bis(aminopropyl) ethylenediamine to bis(aminopropyl) ethylenediamine was 0.205 compared to a ratio of only 0.041 utilizing a cobalt-copper-chromium catalyst.

When the reactor temperature was increased to 135° C. in another run in an attempt to increase conversion here utilizing the cobalt catalyst, while conversion was increased to 88%, the ratio of aminoethyl bis(aminopropyl) ethylene diamine to bis(aminopropyl) ethylenediamine undesirably increased to 0.331 indicating, of course, a even further degree of reaction of stabilizer with product.

EXAMPLE 11

Example 10 was repeated with exception that the catalyst was a 60% nickel catalyst on kieselguhr and the operating temperature was 125° C. While conversion was 90% in terms of biscyano reactant converted the ratio of aminoethyl bis(aminopropyl) ethylene diamine to bis(aminopropyl) ethylenediamine was 0.806. Again, increasing the operating temperature to 135° C., while increasing the conversion of bis(cyanoethyl) ethylenediamine to 98%, nevertheless further increased the aminoethyl bis(aminopropyl) ethylenediamine to bis-(aminopropyl)ethylenediamine ratio to 1.235.

EXAMPLE 12

This example demonstrates that the particular organic amine stabilizer must fall within the defined class here in order to be useful in preventing catalyst pellet disintegration.

Specifically, the procedure of Example 1 was followed with the exception that 1135 g of a feedstock was diluted with 1119 g of triethylamine. 780 g of methanol was employed as solvent, and 1050 g of anhydrous ammonia was employed.

After 56 hours of continuous operation, the catalyst pellets had completely deteriorated. This should be contrasted to the results of Example 1 where excellent catalyst protection was noted.

EXAMPLE 13

Here, again the criticality of the particular amine stabilizer that must be employed was demonstrated. The procedure of Example 2 was followed with exception that benzylamine was employed as a proposed stabilizer in place of the stabilizer-solvent, ethylenediamine used in Example 2. After 94 hours of operation the catalyst pellets had deteriorated significantly. The used catalyst contained many rounded and abraded tablets and a considerable amount of fine particles where noted.

From the foregoing description and examples of this invention, those of ordinary skill in the art may make many modifications and variations therefrom without departing from the scope of the invention as hereinafter claimed.

We claim:

1. A method for preparing polyamines from the corresponding polynitriles using a pelleted cobalt-copper-chromium hydrogenation catalyst which comprises contacting a polynitrile with hydrogen in presence of said catalyst and a stabilizing agent comprising a polyamine wherein said amino groups are separated by four or less carbon atoms or a hydroxyl-amine wherein said amino and hydroxyl groups are separated by four or less carbon atoms whereby catalyst pellet disintegration is inhibited by the presence of said stabilizing agent.

2. The method of claim 1 wherein said stabilizing agent is ethylenediamine.

3. The method of claim 1 wherein said polynitrile is N,N'-bis(cyanoethyl) ethylenediamine.

4. The method of claim 1 wherein said hydrogenation is effected in presence of a solvent.

5. The method of claim 4 wherein said solvent is an organic solvent.

6. The method of claim 5 wherein said organic solvent is an alcohol.

7. The method of claim 6 wherein said alcohol is methanol.

8. The method of claim 1 wherein said stabilizing agent is ethanolamine.

9. The method of claim 1 wherein said polynitrile is an oxypolynitrile.

10. A method of claim 1 wherein said hydrogenation is carried out in presence of ammonia.

11. A method for preparing polyamines from corresponding polynitriles using a pelleted cobalt-copper-chromium hydrogenation catalyst which comprises contacting in liquid phase a polynitrile with said catalyst under reaction conditions including a temperature within the range of from about 80° to about 200° C. and a pressure of about 30 to 800 atmospheres in the additional presence of hydrogen, from about 2 to about 20 moles of ammonia per mol equivalent of nitrile, and a stabilizing agent comprising a polyamine wherein said amino groups are separated by four or less carbon atoms or a hydroxyl-amine wherein said amino and said hydroxyl groups are separated by four or less carbon atoms whereby catalyst pellet disintegration is inhibited by the presence of said stabilizing agent.

12. The method of claim 11 wherein said stabilizing agent is ethylenediamine.

13. The method of claim 11 wherein said polynitrile is N,N'-bis(cyanoethyl) ethylenediamine.

14. The method of claim 11 wherein said hydrogenation is effected in presence of a solvent.

15. The method of claim 14 wherein said solvent in an alcohol.

16. The method of claim 11 wherein said stabilizing agent is ethanolamine.

17. The method of claim 11 wherein said polynitrile is an oxypolynitrile.

18. The method of claim 11 wherein said catalyst comprises cobalt, copper and chromium metal oxides having about 50 percent to about 80 percent cobalt, about 10 percent to about 49 percent copper, and about 1 percent to about 10 percent chromium, based on the total weight of said metals.

* * * * *